United States Patent

Roth et al.

[11] Patent Number: 5,882,485
[45] Date of Patent: *Mar. 16, 1999

[54] PROCESS FOR THE SEPARATION OF DIMETHYL ETHER AND CHLOROMETHANE IN MIXTURES

[75] Inventors: Peter Roth, Eppstein; Erhard Leistner, Braunfels; Hans Haverkamp, Eppstein; Wolfgang Wendel, Kelkheim; Michael Kleiber, Frankfurt, all of Germany

[73] Assignee: Hoechst Aktiengesellschaft, Germany

[ * ] Notice: The term of this patent shall not extend beyond the expiration date of Pat. No. 5,843,286.

[21] Appl. No.: 880,338

[22] Filed: Jun. 23, 1997

[30] Foreign Application Priority Data

Jun. 25, 1996 [DE] Germany ............ 196 25 284.9

[51] Int. Cl.⁶ .............. B01D 3/40; C07C 41/42; C07C 17/386
[52] U.S. Cl. .............. 203/14; 203/23; 203/51; 203/59; 203/60; 203/61; 203/62; 203/63; 203/64; 203/66; 203/67; 203/68; 203/69; 203/70; 203/78; 203/79; 203/80; 203/DIG. 8; 568/699; 570/262
[58] Field of Search .......... 203/14, 23, 78–80, 203/51–57, 92–96, DIG. 8, 60–64, 67–69, 27, 70, 59, 66; 568/699; 570/262

[56] References Cited

U.S. PATENT DOCUMENTS

| | | |
|---|---|---|
| 2,421,441 | 6/1947 | Thronson et al. |
| 3,847,756 | 11/1974 | Statman et al. ............ 203/92 |
| 3,983,180 | 9/1976 | Habata et al. ............ 570/258 |
| 4,334,964 | 6/1982 | Prezelj et al. ............ 203/14 |
| 4,349,416 | 9/1982 | Brandt et al. ............ 203/DIG. 13 |
| 4,474,647 | 10/1984 | Asselinqau et al. ............ 203/94 |
| 4,544,776 | 10/1985 | Osterburg et al. ............ 568/697 |
| 4,560,807 | 12/1985 | Murai et al. ............ 568/698 |
| 4,794,204 | 12/1988 | Pose et al. ............ 570/262 |
| 5,037,511 | 8/1991 | Dornhagen et al. ............ 203/96 |
| 5,092,966 | 3/1992 | Berg et al. ............ 203/57 |
| 5,122,236 | 6/1992 | Smith, Jr. et al. ............ 203/92 |
| 5,132,476 | 7/1992 | Osterbury et al. ............ 570/258 |
| 5,430,197 | 7/1995 | Jones, Jr. ............ 568/697 |
| 5,609,734 | 3/1997 | Streicher et al. ............ 203/98 |

OTHER PUBLICATIONS

Database WPI Section Ch, Week 8036, Derwent Publication Ltd., London, GB & DD 142 183 A (Berger K H), Jun. 11, 1980.

*Primary Examiner*—Virginia Manoharan
*Attorney, Agent, or Firm*—Connolly & Hutz

[57] ABSTRACT

A process for the separation of dimethyl ether and chloromethane in mixtures

A process for the separation of dimethyl ether and chloromethane in mixtures by two distillation steps. In the first step, the mixture is subjected to an extractive distillation with water, aqueous salt solutions or organic liquids as extractant, the top product being chloromethane. In the second step, the dimethyl ether is separated from the extractant.

13 Claims, 1 Drawing Sheet

PROCESS FOR THE SEPARATION OF DIMETHYL ETHER AND CHLOROMETHANE IN MIXTURES

DESCRIPTION

A process for the separation of dimethyl ether and chloromethane in mixtures

The present invention relates to a process for the separation of dimethyl ether (DME) and chloromethane (CM) in mixtures.

Chloromethane is industrially important as starting material for the preparation of chlorofluorocarbons which are then used, for example, as propellant gases. Dimethyl ether is increasingly being used as propellant in spray cans because it is halogen-free and thus has less potential to degrade ozone.

The reactions resulting in dimethyl ether and chloromethane take place under very similar conditions:

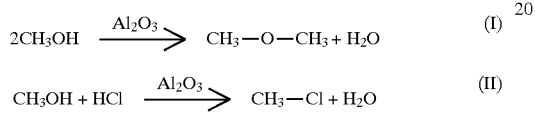

In the preparation of chloromethane which, as shown in equation (II), can take place, for example, on $\gamma$-$Al_2O_3$ catalysts, there is always also formation of dimethyl ether as shown in equation (I). The chloromethane/dimethyl ether mixture produced in this way cannot be worked up by distillation according to the prior art because the boiling points of the components (dimethyl ether: boiling point=−24.9° C., chloromethane: boiling point=−23.7° C.) are very close to one another, and the components moreover form an azeotrope.

The mixture of dimethyl ether and chloromethane has hitherto been worked up to isolate pure chloromethane by hydrolyzing the dimethyl ether with sulfuric acid, which meant that this valuable byproduct of the preparation of chloromethane was lost.

The object was thus to develop a separation process for chloromethane/dimethyl ether mixtures to enable both compounds to be isolated in pure form.

This object has been achieved according to the invention by a two-stage distillation process in which an extractant is used in one stage.

The invention thus relates to a process for the separation of chloromethane and dimethyl ether by extractive distillation, which comprises a) feeding a dimethyl ether/chloromethane mixture into an extractive distillation column, b) adding an organic liquid, an aqueous salt solution or water as extractant in the top part of the extractive distillation column, c) taking off chloromethane vapor at the top of the extractive distillation column, d) taking off a mixture of dimethyl ether and extractant at the bottom of the extractive distillation column, e) feeding the mixture taken off in step d) into a distillation column, f) taking off dimethyl ether vapor at the top of the distillation column, g) taking off the pure extractant at the bottom of the distillation column and then feeding it again into the extractive distillation column.

Suitable extractants are monohydric alcohols, polyhydric alcohols, alkanes, olefins, naphthenes, aromatic compounds, carboxylic acids, ethers, aldehydes, ketones, esters, amines, nitriles or halogenated hydrocarbons, in particular hexane, heptane, cyclohexane, benzene, methanol, acetic acid, dipropyl ether, furfurol, ethyl acetate, triethylamine, acetonitrile, chloroform, and water or aqueous salt solutions, and mixtures thereof.

The distillation columns can be of any suitable design, and packed columns are preferably used. The extractive distillation is preferably carried out under pressures between 1 and 25 bar.

In a preferred embodiment of the invention, the mixture mentioned in step e) is, before being fed into the distillation column, passed through a heat exchanger in which it is heated. It is likewise preferred for the extractant mentioned in step g) to be precooled through said heat exchanger, and to cool it to a temperature which is as low as possible using a cooler before the feeding into the extractive distillation column.

BRIEF DESCRIPTION OF THE DRAWING

FIG. 1 shows a flow diagram of a preferred embodiment of the process according to the invention, which is explained in detail below. A mixture of chloromethane and dimethyl ether (1) is fed through line (2) into an extractive distillation column (3) in which chloromethane and dimethyl ether are separated. The cold extractant, which is preferably at a temperature between 5° and 50° C., is added through line (34) to the top part of the extractive distillation column (3). Suitable extractants are, besides water, all organic liquids whose boiling point under atmospheric pressure is at least 80 K higher than the boiling point of dimethyl ether under atmospheric pressure, and which undergo no chemical reactions either with chloromethane or with dimethyl ether. Addition of the extractant to the extractive distillation column (3) results in precipitation of dimethyl ether in the bottom, and chloromethane is taken off as vapor at the top and can be passed through line (6) into a condenser (7) where it can be precipitated. If an extractant which is immiscible with chloromethane is used, such as, for example, water, the condensate from the condenser (7) can be passed through line (8) into a phase separator (9). The chloromethane phase passes from there through line (11) to the product store (12). The second phase, which can be, for example, an aqueous phase, can be returned from the phase separator (9) through line (10) to the extractive distillation column (3) in order to be reused as extractant. If an extractant which is miscible with chloromethane is used, or if the concentration of extractant in the chloromethane is unimportant, then the phase separator (9) is omitted.

Figure 1:
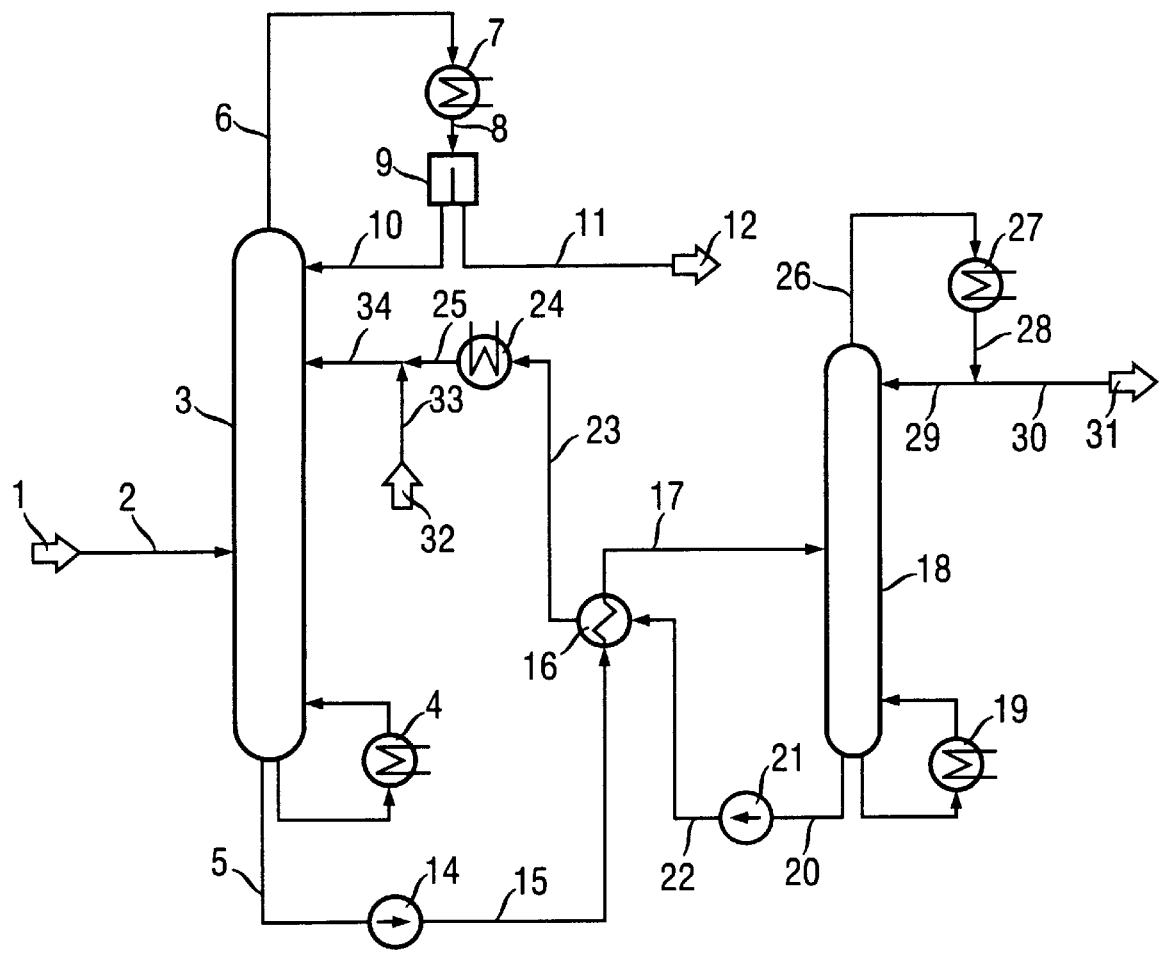
FIG. 1 is a diagrammatic view of a preferred embodiment according to the present invention.

In this case, the product reflux into the extractive distillation column (3) can be adjusted so that the top product is chloromethane of maximum purity.

The mixture of dimethyl ether and the extractant collects in the bottom of the extractive distillation column (3), which is heated by the vaporizer (4). This mixture is passed through line (5) to the pump (14), from there through line (15) where appropriate to the heat exchanger (16), and from there through line (17) to the distillation column (18). Dimethyl ether is separated from the extractant in distillation column (18). Dimethyl ether vapor is taken off at the top through line (26) and can be precipitated in the condenser (27). The condensate can in part be returned through line (28) and (29) into the distillation column (18), otherwise it is transferred through line (28) and (30) into the product store (31). The bottom product in the distillation column (18), which is heated by the vaporizer (19), is the extractant. This can be fed through line (20), the pump (21) and line (22) for cooling to the heat exchanger (16), from where it can be passed through line (23) into a cooler (24), in order from there to be added again to the extractive distillation column (3) through lines (25) and (34). Fresh extractant (32) to compensate losses is fed through line (33).

The process can be carried out in all parts of the system both under atmospheric pressure and under elevated pressure. The procedure under pressures between 1 and 25 bar is preferred because, otherwise, a low temperature is needed to condense the distillates because of the low boiling points of dimethyl ether and chloromethane.

EXAMPLE

A product mixture consisting of 1.8 t/h dimethyl ether and 7.3 t/h chloromethane is fed into an extractive distillation column (3). This extractive distillation column is operated under 10 bar, which means that chloromethane can be condensed at 40° C. The extractant is water, which is fed at 36 t/h and at 35° C. into the extractive distillation column (3). Under the prevailing conditions, the boiling point of the bottom product in the extractive distillation column (3) is 124° C. The chloromethane content dissolved in the extractant is stripped out in the lower part of the column. The bottom product consists of 1.8 t/h dimethyl ether and 36 t/h extraction water, and the chloromethane content in the product stream is 1 ppm. The top product from the extractive distillation is 7.3 t/h chloromethane, the dimethyl ether content in this case being less than 20 ppm. The discharge from the bottom of the extractive distillation column is fed into the distillation column (18) where dimethyl ether and extraction water are separated. The top product in this case is 1.8 t/h dimethyl ether at a temperature of about 40° C. The chloromethane content is about 20 ppm in this case because all the chloromethane in the discharge from the bottom of the extractive distillation column (3) is transferred into the dimethyl ether. The bottom product from the distillation column (18) consists of pure extraction water at a temperature of about 170° C. and is, after cooling to 35° C., again fed into the extractive distillation column (3).

We claim:

1. A process for the separation of chloromethane and dimethyl ether by extractive distillation, which comprises
   a) feeding a dimethyl ether/chloromethane mixture into an extractive distillation column,
   b) adding an organic liquid, an aqueous salt solution or water as extractant in the top part of the extractive distillation column,
   c) taking off chloromethane vapor at the top of the extractive distillation column,
   d) taking off a mixture of dimethyl ether and extractant at the bottom of the extractive distillation column,
   e) feeding the mixture taken off in step d) into a distillation column,
   f) taking off dimethyl ether vapor at the top of the distillation column,
   g) taking off the extractant at the bottom of the distillation column and then feeding it again into the extractive distillation column.

2. The process as claimed in claim 1, wherein the extractant added in step b) comprises monohydric alcohols, polyhydric alcohols, alkanes, olefins, naphthenes, aromatic compounds, carboxylic acids, ethers, aldehydes, ketones, esters, amines, nitriles, halogenated hydrocarbons or mixtures thereof.

3. The process as claimed in claim 1, wherein the extractant added in step b) is hexane, heptane, cyclohexane, benzene, methanol, acetic acid, dipropyl ether, furfurol, ethyl acetate, triethylamine, acetonitrile, chloroform or mixtures thereof.

4. The process as claimed in claim 1, wherein the extractive distillation is carried out under pressures between 1 and 25 bar.

5. The process as claimed in claim 1, wherein the vapors taken off in steps c) and f) are condensed.

6. The process as claimed in claim 1, wherein all the columns used are packed columns.

7. The process as claimed in claim 1, wherein the extractant in step b) is fed at a temperature between 5° and 50° C. into the extractive distillation column.

8. The process as claimed in claim 1, wherein the mixture in step e) is preheated before being fed into the distillation column, and wherein the extractant in step g) is cooled before being fed into the extractive distillation column.

9. The process as claimed in claim 8, wherein the mixture in step e) is preheated in a heat exchanger, and wherein the extractant in step g) is precooled through the heat exchanger and cooled through a cooler.

10. The process as claimed in claim 1, wherein
    chloromethane and the extractant are immiscible, the vapor taken off in step c) is condensed, the condensate is separated in a phase separator, the extractant is returned to the extractive distillation column, and the remaining chloromethane is taken off.

11. The process as claimed in claim 10 wherein the vapor taken off in step f) is condensed and part of the condensate produced is fed to the top of the distillation column.

12. The process as claimed in claim 1 wherein chloromethane and the extractant are miscible, the vapor taken off in step c) is condensed, and part of the condensate obtained is returned to the extractive distillation column.

13. The process as claimed in claim 12 wherein the vapor taken off in step f) is condensed and part of the condensate produced is fed to the top of the distillation column.

* * * * *

UNITED STATES PATENT AND TRADEMARK OFFICE
CERTIFICATE OF CORRECTION

PATENT NO. : 5,882,485
DATED : March 16, 1999
INVENTOR(S) : Peter Roth ET AL.

It is certified that error appears in the above-identified patent and that said Letters Patent is hereby corrected as shown below:

Column 4, line 12, "nitrites" should read -- nitriles --.

Signed and Sealed this

Twenty-seventh Day of July, 1999

Attest:

Q. TODD DICKINSON

*Attesting Officer*   Acting Commissioner of Patents and Trademarks